United States Patent [19]

Scheirer

[11] Patent Number: 5,618,682
[45] Date of Patent: Apr. 8, 1997

[54] BIOLUMINESCENCE MEASUREMENT SYSTEM

[75] Inventor: Winfried Scheirer, Wienergasse, Austria

[73] Assignee: Packard Instrument Co., Inc., Downers Grove, Ill.

[21] Appl. No.: 193,679

[22] Filed: Feb. 8, 1994

[30] Foreign Application Priority Data

Feb. 10, 1993 [AT] Austria .................................... 243/93

[51] Int. Cl.$^6$ ............................... C12Q 1/66; G01N 21/00
[52] U.S. Cl. ....................... 435/8; 435/4; 435/6; 435/184; 435/968; 436/35; 436/164; 436/166; 436/172
[58] Field of Search .............................. 435/8, 4, 6, 184, 435/968; 436/35, 164, 166, 172

[56] References Cited

U.S. PATENT DOCUMENTS

| | | | |
|---|---|---|---|
| 4,235,961 | 11/1980 | Lundin | 435/8 |
| 4,246,340 | 1/1981 | Lundin et al. | 435/8 |
| 4,665,022 | 5/1987 | Schaeffer et al. | 435/8 |
| 5,283,179 | 2/1994 | Wood | 435/8 |

FOREIGN PATENT DOCUMENTS

| | | |
|---|---|---|
| 243/93 | 2/1993 | Austria . |
| 0022757 | 1/1981 | European Pat. Off. . |
| 0299601 | 1/1989 | European Pat. Off. . |
| 0516443 | 2/1992 | European Pat. Off. . |
| WO92/04468 | 3/1992 | WIPO . |

OTHER PUBLICATIONS

Webster et al, *Chemical Abstracts*, vol. 95, p. 299, Ref. #57468z, 1981 (Int. Symp. Anal. Appl. Biolumin Chemilumin. 2nd 1980, 497–504, 1981).

Rhodes et al, *J. Biol. Chem*, vol. 233, pp. 1528–1537, 1958.

Gunther et al, *Eur. J. Biochem*, vol. 202, pp. 507–513, 1991.

Wood, Chemical Abstracts, vol. 117, p. 365, Ref. #127363k, 1992 (Biolumin Chemilumin. Proc. Symp. 6th, 11–14, 1990).

Protocols and Information for Measuring Firefly Luciferase Expressed in Cells, *Luciferase Assay Guide Book*, Analytical Luminescence Laboratory, 1992.

Scheirer et al., A Convenient System for the Serial Quantitation of Viable Cells Measuring Luminescence of ATP, *Develop. Biol. Standard*, 66:349–355, 1985.

Thompson et al., Modulation of Firefly Luciferase Stability and Impact on Studies of Gene Regulation, *Gene*, 103:171–177, 1991.

I Bjorkhem et al. "A simple, fully enzymic bioluminenscent assay for triglycerides in serum", Clinical Chemistry, vol. 28, No. 8, pp. 1742–1744 (Aug. 1982).

*Primary Examiner*—Elizabeth C. Weimar
*Assistant Examiner*—Abdel A. Mohamed
*Attorney, Agent, or Firm*—Arnold, White & Durkee

[57] ABSTRACT

The present invention provides a method of increasing the duration of detectable photon emission of a luciferase-luciferin reaction. The method provides a luciferase-luciferin reaction in which photon emission can be detected for up to and including eight hours. A method of the present invention can also be used to detect the presence of luciferase in biological samples. The present invention also provides a composition used in detecting the presence of luciferase in biological samples.

25 Claims, 7 Drawing Sheets

BIOLUMINESCENCE MEASUREMENT SYSTEM

FIELD OF THE INVENTION

This invention relates generally to the stabilization of luciferase catalyzed luminescence. The invention relates as well to compositions and methods for improving the lifetimes of the luminescence reaction. This invention also includes assay kits for detection of an expressed luciferase gene used in reporter-gene techniques.

BACKGROUND OF THE INVENTION

Luciferases are found in a wide variety of organisms including fireflies, photobacteria, jellyfish and many others. Luciferases are enzymes which catalyze the production of light by oxidizing luciferin to oxyluciferin in a process known generally as bioluminescence.

The production of photons by luciferase occurs through a two step reaction which consumes luciferin, adenosine triphosphate (ATP) and $O_2$. In the first step, luciferase catalyzes the formation of luciferyl adenylate from luciferin and ATP. In this first step pyrophosphate is released and a $Mg^{+2}$ cofactor or another divalent cation is required for proper luciferase function. Upon formation, luciferyl adenylate remains within the active site of luciferase. In the next step, luciferase oxidizes luciferyl adenylate to an electronically excited oxyluciferin with the consumption of oxygen. Light production occurs when the electronically excited oxyluciferin decays to the ground state oxyluciferin. The decay from the excited state to the ground state occurs with the concomitant emission of a photon. The color of the light produced differs with the source of the luciferase and appears to be determined by differences in the structure of the various luciferases.

Luciferases have recently become useful in reporter-gene technology. In this technique, a reporter gene, such as a luciferase encoding polynucleotide is used as an indicator for the transcription and translation of a gene in a cellular expression system. The reporter gene is operatively linked to a promoter that is recognized by the cellular expression system. Other commonly used reporter genes include β-galactosidase, and chloramphenicol acetyltransferase (CAT). In a typical reporter gene assay, a DNA vector containing the reporter gene is transfected into a cell capable of expressing the reporter gene. After a sufficient amount of time to allow for the expression of the reporter gene has passed, the cellular membrane is disrupted to release the expressed gene product. The reagents necessary for the catalytic reaction of the reporter gene are then added to the reaction solution and the enzymatic activity of the reporter gene is determined. Alternatively, the cell can be disrupted in the presence of all reagents necessary for the determination of the enzymatic activity of the reporter gene. If a β-galactosidase encoding polynucleotide is used as the reporter gene, the hydrolysis of a galactoside is determined. If a chloramphenicol acetyltransferase encoding polynucleotide is used as the reporter gene, the production of an acetylated chloramphenicol is determined. When luciferase is used as the reporter gene the photons produced from the luciferase-luciferin reaction is measured.

A major problem in determining expression of a luciferase gene as a reporter gene is the short duration of photon production. Typically, luciferase catalyzed photon production ceases within a few seconds. Means for extending the period of photon production have been eagerly sought. Currently a commercially available kit from the Promega Corporation (Madison, Wis.) can extend the half-life of luciferase catalyzed photon production to roughly five minutes. Nevertheless, for the measurement of large numbers of samples, luciferase catalyzed photon production with a half-life of only five minutes is not a viable alternative. As used herein, half-life is the time it takes for photon production to decrease by one half.

The present invention provides methods and compositions for increasing the duration of detectable photon emission of a luciferase-luciferin reaction.

BRIEF SUMMARY OF THE INVENTION

In one aspect, the present invention provides a method for increasing the duration of detectable photon emission of a luciferase-lucifefin reaction. In one embodiment, a reaction mixture containing luciferase, luciferin, ATP, and cofactors required for luciferase catalytic activity is mixed with a composition containing adenosine monophosphate, a radical scavenger and a chelating agent to form an admixture. The photons produced by the luciferase-luciferin reaction is then detected by measuring the luminescence of the admixture. The luciferase catalyzed photon production can be detected for more than five minutes.

In a preferred embodiment, 100 ml of the admixture contains about 2.8 mg luciferin, about 110 mg adenosine triphosphate (ATP), cofactors necessary for luciferase catalytic activity, about 2.2 mg adenosine monophosphate (AMP), about 385 mg dithiothreitol (DTT), and about 20 mg ethylenediaminetetraacetic acid (EDTA).

In another embodiment, the amount of one of the components of the admixture can be varied while the amounts of all other components remain unchanged. For example, in 100 ml of the admixture, the amount of luciferin can be varied between about 0.2 to about 30 mg while maintaining the amount of ATP at about 110 mg, AMP at about 2.2 mg, DTT at about 385 mg and EDTA at about 20 mg. Similarly, components can be varied individually as follows: for 100 ml of the admixture, the amount of luciferin can be varied from about 0.2 to about 30 mg; the amount of ATP can be varied from about 10 to about 300 mg; the amount of AMP can be varied from about 0.2 to about 30 mg; the amount DTT can be varied from about 200 to about 2000 mg; and the amount of EDTA can be varied from between about 10 to about 50 mg.

In another embodiment, the present invention contemplates a method for detecting the presence of luciferase in a biological sample. The biological sample suspected of containing luciferase is mixed with a reaction mixture which contains luciferin, adenosine triphosphate, cofactors required for luciferase catalytic activity, adenosine monophosphate, dithiothreitol, ethylenediaminetetraacetic acid, phenylacetic acid, oxalic acid, and a detergent to form an admixture. The photons produced by the luciferase-luciferin reaction are then detected by measuring the luminescence of the admixture.

In a preferred embodiment, the present invention contemplates an admixture for detecting the presence of a luciferase in a biological sample. One hundred ml of the admixture contains about 2.8 mg luciferin, about 110 mg adenosine triphosphate, about 2.2 mg adenosine monophosphate, about 385 mg dithiothreitol, about 20 mg ethylenediaminetetraacetic acid, about 4.5 mg phenylacetic acid, and about 0.85 mg oxalic acid.

In another embodiment, the amount of one of the components of the admixture can be varied while the amounts of all other components remain unchanged. For example, in 100 ml of the admixture, the amount of luciferin can be varied between about 0.2 to about 30 mg while maintaining the amount of ATP at about 110 mg, AMP at about 2.2 mg, DTT at about 385 mg, EDTA at about 20 mg, phenylacetic acid at about 4.5 mg, and oxalic acid at about 0.85 mg. Similarly, components can be varied individually as follows: for 100 ml of the admixture, the amount of luciferin can be varied from about 0.2 to about 30 mg; the amount of ATP can be varied from 10 to about 300 mg; the amount of AMP can be varied from about 0.2 to about 30 mg; the amount DTT can be varied from about 200 to about 2000 mg; the amount of EDTA can be varied from about 10 to about 50 mg; the amount of phenylacetic acid can be varied from about 1 to about 10 mg; and the amount of oxalic acid can be varied from about 0.2 to about 5 mg.

In another aspect, the present invention contemplates a composition used in detecting the presence of luciferase in biological samples by detecting an emitted photon from a luciferase-luciferin reaction. One hundred ml of this composition contains about 2.8 mg luciferin, about 110 mg adenosine triphosphate, about 2.2 mg adenosine monophosphate, about 385 mg dithiothreitol, about 20 mg ethylenediaminetetraacetic acid, about 4.5 mg phenylacetic acid, about 0.85 mg oxalic acid, and about 4 g. Triton (a registered trademark of Union Carbide Chemicals and Plastics Co., Inc.)

BRIEF DESCRIPTION OF THE INVENTION

DETAILED DESCRIPTION OF THE INVENTION

Luciferases catalyze the oxidation of luciferin with the concomitant emission of photons. The present invention provides compositions and methods for increasing the duration of detectable photon emission of a luciferase-luciferin reaction. The present invention provides a luciferase-luciferin reaction in which light production can be detected for more than five minutes. In a preferred embodiment, the photon emission of a luciferase-luciferin reaction can be detected for up to and including eight hours. In another embodiment, detectable photon emission from a luciferase-luciferin reaction is linear for up to eight hours (see FIGS. 1–5).

Figure 1:
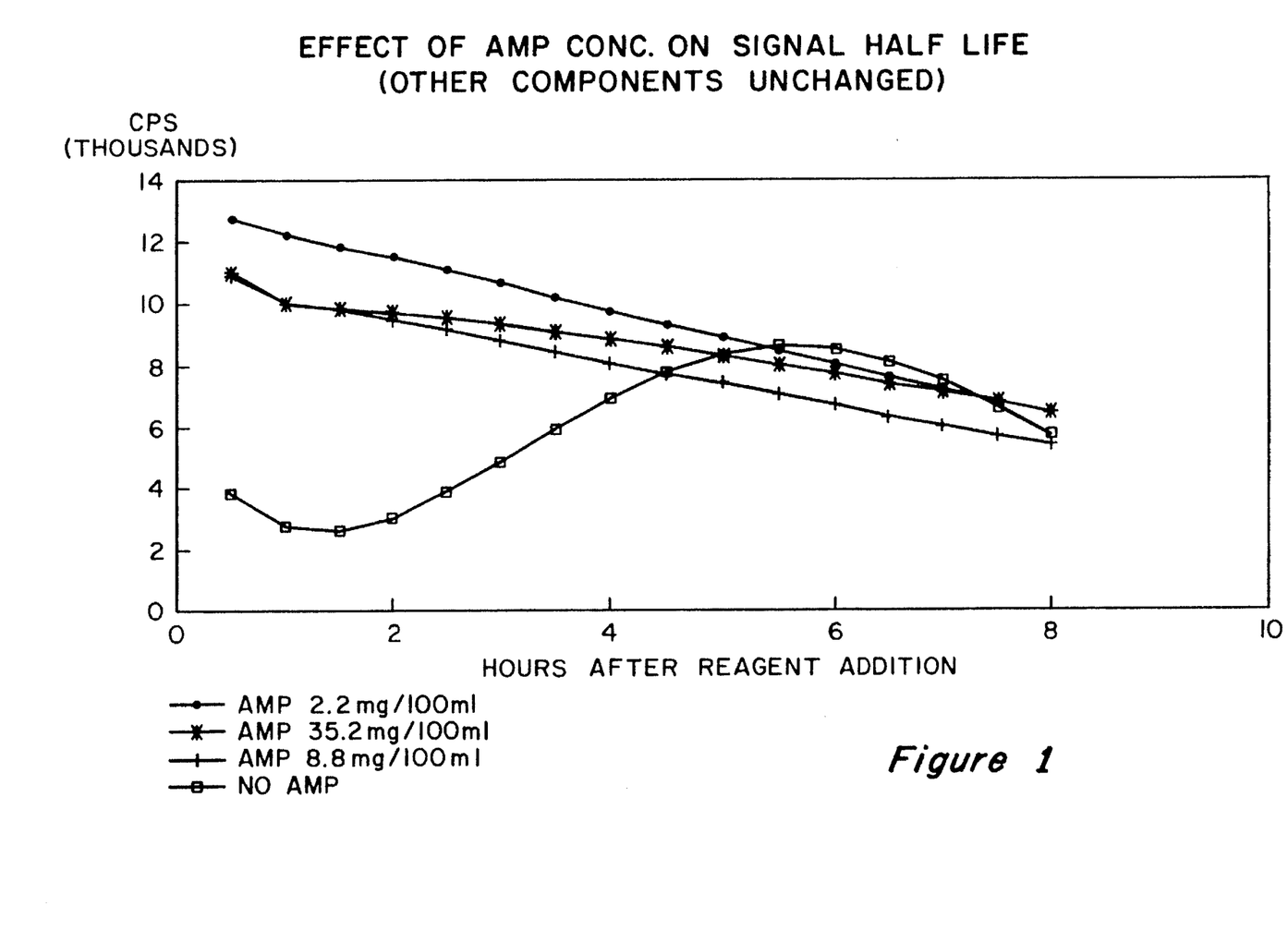
FIG. 1 shows the effect of varying the AMP concentration on luciferase-luciferin light production.
Figure 2:
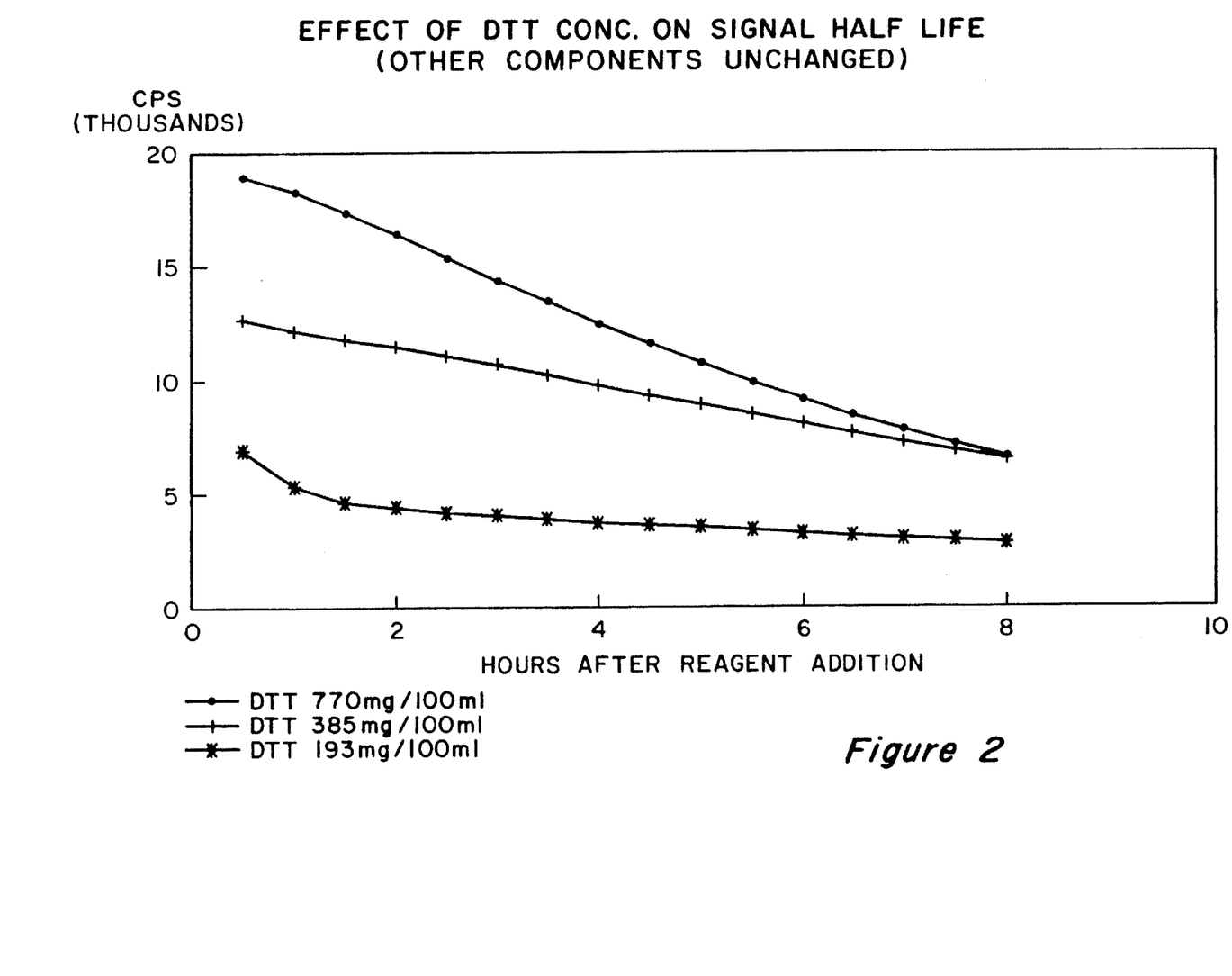
FIG. 2 shows the effect of varying DTT concentration on luciferase-luciferin light production.
Figure 3:
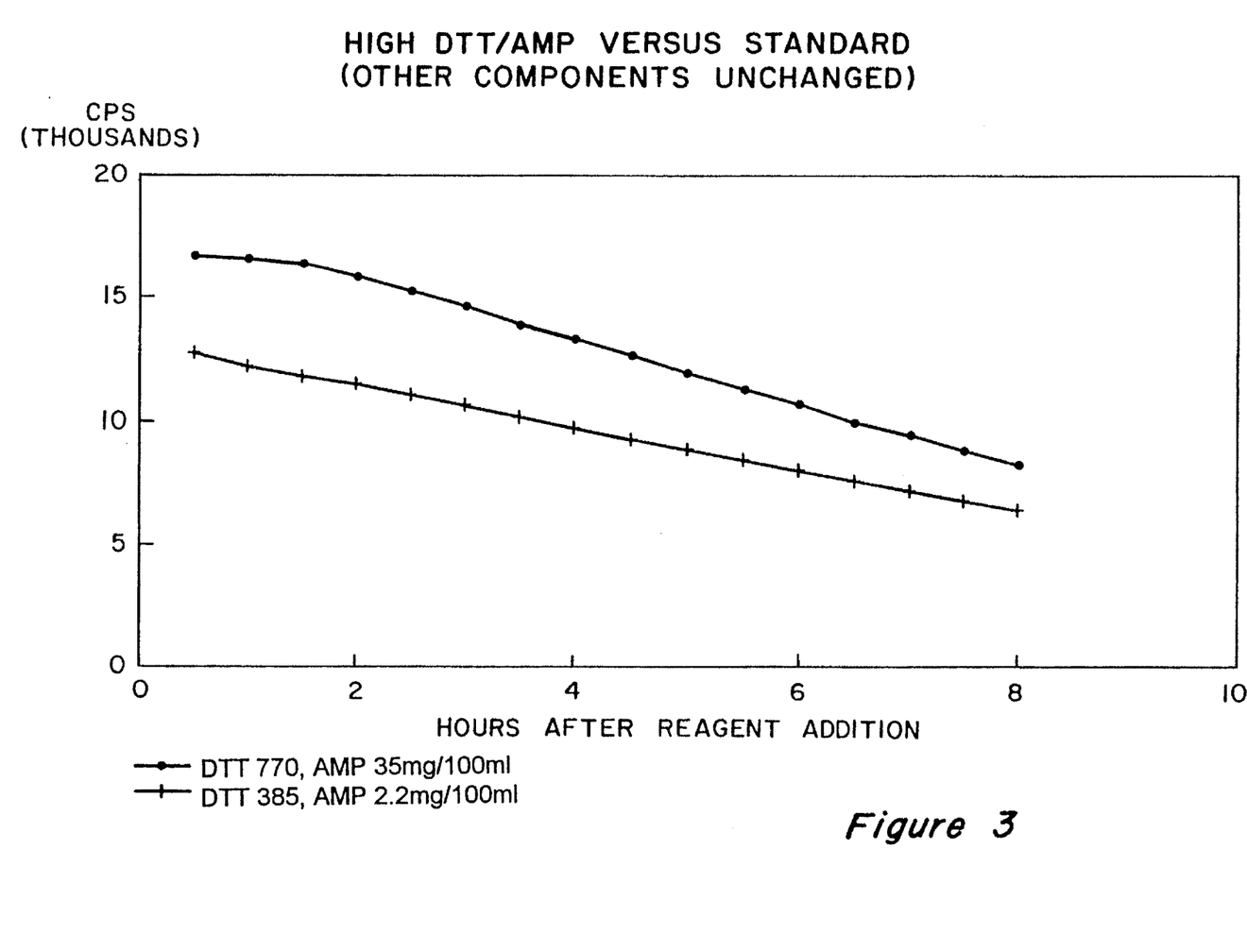
FIG. 3 shows the effect of varying both DTT and AMP concentration on luciferase-luciferin light production.

In one embodiment, a reaction mixture containing luciferase, luciferin, ATP, and cofactors required for luciferase catalytic activity is mixed with a composition containing adenosine monophosphate, a radical scavenger and a chelating agent to form an admixture. The photons produced by the luciferase-luciferin reaction are then detected by measuring the luminescence of the admixture. Luciferase catalyzed photon emission as disclosed by the methods and compositions of the present invention can be detected for more than five minutes. In a preferred embodiment, photon emission can be detected for more than thirty minutes and for up to eight hours. In a preferred embodiment, photon emission decays linearly for up to eight hours as shown in FIGS. 1–3.

In a preferred embodiment, the present invention provides a luciferase-luciferin reaction admixture. One hundred ml of the admixture contains about 2.8 mg luciferin, about 110 mg adenosine triphosphate, about 2.2 mg adenosine monophosphate, about 385 mg dithiothreitol, and about 20 mg ethylenediaminetetraacetic acid.

In another embodiment, the amount of one of the components of the admixture can be varied while the amounts of all other components remain unchanged. For example, in 100 ml of the admixture, the amount of luciferin can be varied between about 0.2 to about 30 mg while maintaining the amount of ATP at about 110 mg, AMP at about 2.2 mg, DTT at about 385 mg and EDTA at about 20 mg. Similarly, components can be varied individually as follows: for 100 ml of the admixture, the amount of luciferin can be varied from about 0.2 to about 30 mg; the amount of ATP can be varied from about 10 to about 300 mg; the amount of AMP can be varied from about 0.2 to about 30 mg; the amount DTT can be varied from about 200 to about 2000 mg; and the amount of EDTA can be varied from between about 10 to about 50 mg. As an example, the present invention contemplates an admixture of the following composition: 100 ml of the admixture contains about 2.8 mg luciferin, about 110 mg adenosine triphosphate, between about 0.2 to about 35 mg adenosine monophosphate, about 385 mg dithiothreitol, and about 20 mg ethylenediaminetetraacetic acid. Other admixtures in which only one component is varied in accordance with the limitations disclosed above are contemplated.

In another aspect, the present invention contemplates a method for detecting the presence of luciferase in a biological sample. The biological sample suspected of containing luciferase is mixed with a reaction mixture which contains luciferin, adenosine triphosphate, cofactors required for luciferase catalytic activity, adenosine monophosphate, dithiothreitol, ethylenediaminetetraacetic acid, phenylacetic acid, oxalic acid, and a detergent to form an admixture. The photons produced by the luciferase-luciferin reaction is then detected by measuring the luminescence of the admixture. A preferred biological sample is a cell that produces luciferase. An exemplary detergent is Triton® N-101 (nonylphenoxypolyethoxyethanol). The present invention provides methods and compositions in which the presence of luciferase in the biological sample can be detected for more than five minutes by detection of the emitted photon. In a preferred embodiment, photon emission can be detected for more than thirty minutes and for up to eight hours. In a preferred embodiment, photon emission decays linearly for up to eight hours as shown in FIGS. 1–3.

In a preferred embodiment, the present invention contemplates an admixture for detecting the presence of luciferase in a biological sample. One hundred ml of the admixture contains about 2.8 mg luciferin, about 110 mg adenosine triphosphate, about 2.2 mg adenosine monophosphate, about 385 mg dithiothreitol, about 20 mg ethylenediaminetetraacetic acid, about 4.5 mg phenylacetic acid, about 0.85 mg oxalic acid, and a detergent.

In another embodiment, the amount of one of the components of the admixture can be varied while the amounts of all other components remain unchanged. For example, in 100 ml of the admixture, the amount of luciferin can be varied between about 0.2 to about 30 mg while maintaining the amount of ATP at about 110 mg, AMP at about 2.2 mg, DTT at about 385 mg, EDTA at about 20 mg, phenylacetic acid at about 4.5 mg, and oxalic acid at about 0.85 mg. Similarly, components can be varied individually as follows: for 100 ml of the admixture, the amount of luciferin can be varied from about 0.2 to about 30 mg; the amount of ATP can be varied from about 10 to about 300 mg; the amount of AMP can be varied from about 0.2 to about 30 mg; the amount DTT can be varied from about 200 to about 2000 mg; the amount of EDTA can be varied from about 10 to about 50 mg; the amount of phenylacetic acid can be varied from about 1 to about 10 mg; and the amount of oxalic acid can be varied from about 0.2 to about 5 mg.

In another aspect, the present invention contemplates a composition used in detecting the presence of luciferase in biological samples by detecting emitted photons from a luciferase-luciferin reaction. One hundred ml of this composition contains about 2.8 mg luciferin, about 110 mg adenosine triphosphate, about 2.2 mg adenosine monophosphate, about 385 mg dithiothreitol, about 20 mg ethylenediaminetetraacetic acid, about 4.5 mg phenylacetic acid, and about 0.85 mg oxalic acid.

In a more preferred embodiment, the present invention contemplates a reaction mixture for detecting the presence of a luciferase in a biological sample, 100 ml of which contains about 2.8 mg luciferin, about 110 mg adenosine triphosphate, about 2.2 mg adenosine monophosphate, about 385 mg dithiothreitol, about 20 mg ethylenediaminetetraacetic acid, about 4.5 mg phenylacetic acid, about 0.85 mg oxalic acid, and a detergent. As an example, the present invention contemplates an admixture of the following composition: 100 ml of the admixture contains about 2.8 mg luciferin, about 110 mg adenosine triphosphate, about 2.2 mg adenosine monophosphate, between about 200 to 2000 mg dithiothreitol, about 20 mg ethylenediaminetetraacetic acid, about 4.5 mg phenylacetic acid, and about 0.85 mg oxalic acid. Other admixtures in which only one component is varied as discussed above are contemplated.

As used herein, the term "luciferase" is an enzyme which catalyzes the oxidation of luciferin with the concomitant emission of a photon. Luciferases can be isolated from biological specimens which produce luciferase or from a cell which has been transformed or transfected with a polynucleotide encoding for a luciferase. It is within the skill of one of ordinary skill in the art to isolate a luciferase from a biological specimen that produces luciferase. Similarly, means of transforming or transfecting a cell with a polynucleotide that encodes for a luciferase are well known in the art.

One aspect of the invention provides a method for increasing the duration of detectable photon emission of a luciferase-luciferin reaction for more than thirty minutes by the addition of certain reagents. A large number of substances which influence the luciferin-luciferase reaction including dithiothreitol, cytidine nucleotides, AMP, pyrophosphate, coenzyme A, EDTA, protease inhibitors, and luciferase inhibitors including luciferin analogs have been reported.

Decomposition and inactivation of luciferase decreases the lifetime of the luciferase-luciferin reaction by inactivation of luciferase. In reporter gene techniques where cell lysates are used, the inactivation of luciferase by endogenous proteases present in the cell lysate is a particular problem. The addition of protease inhibitors such as phenylacetic acid (PAA), oxalic acid, monensine, acetyl phenylalanine, leupeptine, ammonium chloride, aprotinin and others prevent the degradation of luciferase by endogenous proteases present in the biological sample. By slowing down or preventing the inactivation of luciferase, luciferase catalyzed light production is lengthened. The above list is illustrative only and many other protease inhibitors are well known in the art. The use of other protease inhibitors is contemplated by the present invention.

The addition of luciferin analogs and other inhibitors of luciferase increase the lifetime of light production by inhibiting luciferase. Care must be taken to ensure that the inhibitor binds to luciferase reversibly. Analogs that bind irreversibly permanently inhibit luciferase. Exemplary reversible inhibitors of luciferase include phenylbenzothiazol, 2-aminoethanol, benzothiazole, 2-hydroxyphenylbenzothiazole and pyrophosphate.

Adenosine monophosphate (AMP) is a catalytic product of the luciferase-luciferin reaction. The addition of AMP promotes the initial phase of the luciferase luciferin reaction. As shown in FIG. 1, in the absence of AMP, initial photon emission is low and maximum light production occurs nearly six hours after the initiation of the luciferase-luciferin reaction. In contrast, when the concentration of AMP is between about 2.2 and about 35.2 mg/100 ml, maximum light production occurs immediately and decreases in a linear manner for more than eight hours. FIG. 1 shows the effect of varying the AMP concentration on luciferase-luciferin light production. 100 ml of the admixture contained 110 mg adenosine triphosphate, 385 mg dithiothreitol, 2.8 mg luciferin, 20 mg ethylenediaminetetraacetic acid, 4 ml of a 10% Triton® N-101 (nonylphenoxypolyethoxyethanol) solution in $H_2O$, 4.5 mg phenylacetic acid, and 0.85 mg oxalic acid in 50 mM N-[2-hydroxyethyl]piperazine-N'-[2-ethanesulfonic acid] (HEPES), pH, 7.8. The amount of AMP added to 100 ml of the assay solution was varied from about 0 to about 35.2 mg. With the addition of about 8.8 mg and about 35.2 mg of AMP, detectable photon emission was linear between one and eight hours. The addition of 2.2 mg of AMP resulted in photon emission which was linear for up to eight hours.

Thiol compounds such as dithiothreitol (DTT), dithioerythritol, glutathione and other well known reducing agents are radical scavengers and increase the duration of detectable photon emission of a luciferase-luciferin reaction. While the mechanism of thiol compound stabilization of the luciferase-luciferin reaction is not well understood, these compounds probably function by limiting the availability of oxygen necessary in the second step of the luciferase-luciferin reaction. At higher concentrations, DTT increases emission of photons through an unknown mechanism. FIG. 2 shows the effect of varying DTT concentration on luciferase-luciferin light production. in FIG. 2, 100 ml of the assay solution contained 2.2 mg adenosine monophosphate, 110 mg adenosine triphosphate, 2.8 mg luciferin, 20 mg ethylenediaminetetraacetic acid, 4 ml of a 10% Triton® N-101 (nonylphenoxypolyethoxyethanol) solution in $H_2O$, 4.5 mg phenylacetic acid, and 0.85 mg oxalic acid in 50 mM N[2-hydroxyethyl]piperazine-N'-[2-ethanesulfonic acid] (HEPES), pH, 7.8. The amount of DTT in the admixture varied from 193 to 770 mg. The addition of 385 and 770 mg of DTT resulted in detectable photon emission which was linear for up than eight hours. When 193 mg of DTT is added, light production was reduced and was linear between two and eight hours.

FIG. 3 shows the effect of varying both DTT and AMP concentration on the duration of detectable photon emission from a luciferase-luciferin reaction. 100 ml of the admixture contained 110 mg adenosine triphosphate, 2.8 mg luciferin, 20 mg ethylenediaminetetraacetic acid, 4 ml of a 10% Triton® N-101 (nonylphenoxypolyethoxyethanol) solution in $H_2O$, 4.5 mg phenylacetic acid, and 0.85 mg oxalic acid, in 50 mM N[2-hydroxyethyl]piperazine-N'-[2-ethanesulfonic acid](HEPES), pH, 7.8. The addition of 385 mg DTT and 2.2 mg AMP resulted in detectable photon emission which was linear between 1.75 and 8 hours. The addition of 770 mg DTT and 35 mg AMP resulted in detectable photon emission which was linear for up to eight hours.

Chelating agents which bind metal ions can increase the duration of photon emission from a luciferase-luciferin reaction by binding $Mg^{+2}$ and other divalent cations including $Ca^{+2}$, $Fe^{+2}$, $Mn^{+2}$, $Co^{+2}$, and $Zn^{+2}$. In reporter gene techniques, the concentrations of divalent cations cannot be rigorously controlled because whole cell lysates are used. Lysis of cells expressing a luciferase encoding gene release all of the endogenous divalent cations including $Mg^{+2}$ and $Ca^{+2}$ into the luciferase-luciferin reaction admixture. The addition of chelating agents effectively removes the released $Mg^{2+}$ and $Ca^{+2}$. Exemplary chelating agents include ethylenediaminetetraacetic acid (EDTA), and ethylene glycol-bis (β-aminoethyl ether) N,N,N',N',-tetraacetic acid (EGTA). The use of other chelating agents are contemplated by the present invention.

The use of detergents to lyse cells suspected of expressing luciferase is well known in the art. Exemplary anionic detergents include the series of Triton® detergents including Triton® N-101. The substitution of other detergents, including both ionic and anionic detergents is within the skill of an ordinary artisan.

The use of reagents to maintain the pH of the luciferase-luciferin reaction solution is well known in the art. An exemplary buffering reagent is N-[2-hydroxyethyl] piperazine-N'-[2-ethanesulfonic acid] (HEPES). Many other buffering reagents are well known and are commercially available.

Figure 4:
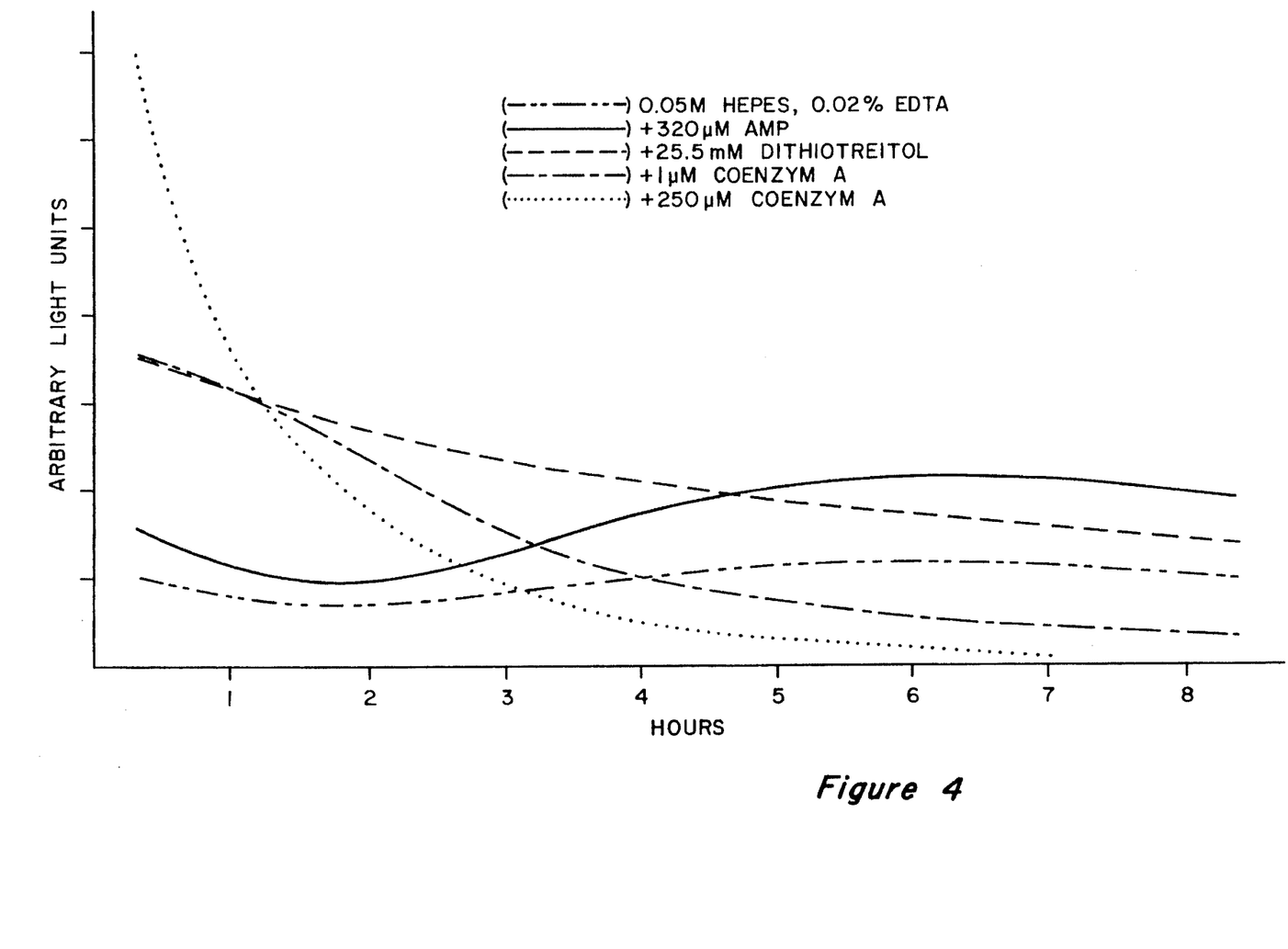
FIG. 4 shows the effect of various reagents to the luciferase-luciferin reaction.

The present invention provides a combination of reagents which increase the duration of detectable photon emission from a luciferase-luciferin reaction. FIG. 4 shows the effect on the lifetime of the luciferase-luciferin reaction in an admixture consisting of luciferase, luciferin, ATP, cofactors required for luciferase catalytic activity and EDTA (20 mg/100 ml) in 50 mM HEPES and AMP, DTT or coenzyme A. In all of the combinations shown in FIG. 4, the detectable photon emission from a luciferase-luciferin reaction lasts for at least for eight hours with the exception of a solution containing EDTA and 250 μM coenzyme A in which photons can be detected for 7 hours.

The linearity in the decrease of photon emission during the life of a luciferase-luciferin reaction is an important aspect of the present invention. Because photon emission is linear during the life of the luciferase-luciferin reaction, initial luminescence can be calculated easily from the luminescence detected at any time during the life of the luciferase-luciferin reaction. From the calculated initial luminescence, the concentration of the luciferase in the measured sample can be determined. For example, in the reporter gene technique, samples suspected of expressing luciferase can be measured over a period of many hours and the initial concentration of luciferase in the samples can be determined.

As discussed below in Examples 1 and 2 the present invention allows for the measurement of large numbers of samples. Recently, instrumentation for measuring photon emission from 96 well microtiter plates became available ("FopCount Microplate Scintillation and Luminescence Counter" from the Packard Instrument Company, Inc. of Downers Grove, Ill.). The light output from each 96 well plate takes roughly ten minutes to measure. Thus with a linear emission of photons of eight hours, forty eight 96-well plates can be easily measured. This results in the measurement of photon emission from 4608 individual samples.

EXAMPLE 1

Reporter-gene Assay Using a Luciferase cDNA

Figure 5:
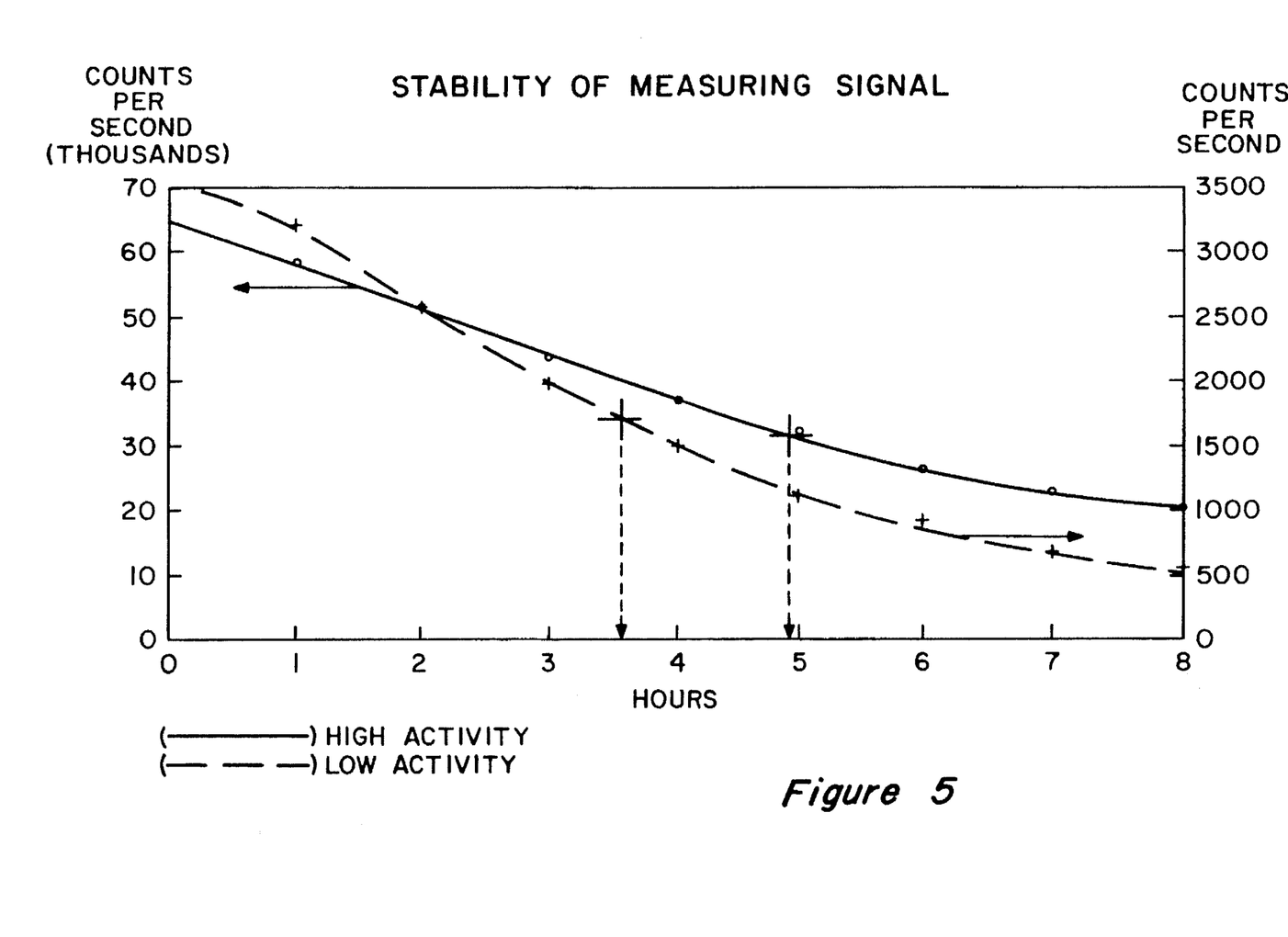
FIG. 5 shows the light production of a reporter-gene assay using a cloned luciferase.

The reporter gene technique using a cloned luciferase was used to demonstrate the increased duration of the luciferase-luciferin reaction. The production of light from transiently transformed human T-cells (Jurkat) was measured for eight hours. Jurkat cells in the logarithmic phase of growth were transformed by the DEAE-dextran technique and incubated in a humidified incubator for 48 hours under assay conditions. The plasmid vector contained a luciferase gene under the control of the EF promoter. After 48 hours, 100 μl of the cell suspension was mixed with 100 μl of PBS and 100 μl of a 100 ml solution containing 2.2 mg adenosine monophosphate, 110 mg adenosine triphosphate, 385 mg dithiothreitol, 2.8 mg luciferin, 20 mg ethylenediaminetetraacetic acid, 4 ml of a 10% Triton® N-101 (nonylphenoxypolyethoxyethanol) solution in $H_2O$, 4.5 mg phenylacetic acid, 0.85 mg oxalic acid, and 50 mM N-[2-hydroxyethyl]piperazine-N'-[2-ethanesulfonic acid](HEPES), pH 7.8. The production of light was then measured for up to eight hours. The "high activity" curve (solid line) represents light production from the transformation of Jurkat cells with 2 μg of the luciferase containing vector at a concentration of $1 \times 10^6$ cells/mi. The "low activity" curve represents light production from the same experiment but with a cellular concentration of 50,000 cells/mi. The half life of the "high activity" sample was found to be roughly 3.5 hours and the half life of the "low activity" curve was found to be roughly 5 hours.

EXAMPLE 2

High-capacity Luciferase Reporter Gene Assay. for HIV-Rev-RRE-Interaction

A transient transfection assay using the DEAE-dextran technique for T-cell lines was established to screen for inhibitors of the HIV-rev regulatory protein (RRE). Two expression vectors, one for the HIV-1 gene (pEF-cRev) and the other for a luciferase reporter gene (pCMV-Luc/RRE) are cotransfected into the Jurkat cell line (lymphoblastoid cells). RRE is expressed together with Luciferase if a certain level of functional rev protein has been accumulated within a cell. The assay mimics the natural action of rev. Rev transports unspliced or singly spliced RRE-containing mRNA out of the nucleus to the translation machinery in the cytoplasm. If a certain threshold level of rev protein accumulates in the nucleus, rev binds to RRE containing mRNA, multimerizes and mediates transport of this mRNA into a cellular pathway bypassing the cellular splicing machinery. This is accomplished by binding of the Rev/RRE complex to a cellular factor, translation initiation factor elF-5a, of the pre-ribosomes formed within the nucleoli. Inhibitors of any of these steps in the mode of action of rev is detectable in this reporter gene assay.

The assay conditions have been optimized to obtain a stimulation of luciferase expression by rev to approx.

20–100 fold over background within 20 hours of transfection. The basal luciferase expression as determined in control transfections with an identical expression vector carrying the rev gene in antisense orientation to the promoter (pEF-AScRev) is usually below 5% of the rev-induced expression. The toxicity of candidate compounds is determined by a parallel transfection assay. In this assay, a rev-independent luciferase construct (pCMV-LUC) is cotransfected with the rev-expression vector (pEF-cRev) to keep conditions similar to the rev-assay. This toxicity assay also identifies compounds which are inhibitors of the luciferase enzyme or to transcription factors binding to the CMV-promoter. Therefore, the toxicity assay is also capable of acting as a specificity control.

The assay has been adapted to microplate technology and can be automated. While detectors to measure multiple samples have been known for some time, modern single photon measurement techniques with an extraordinarily high sensitivity for detection of bioluminescence signals from microplates came to the market recently. The stabilization of the bioluminescence signal from a halflife of a few minutes to more than 4 hours allows for the automation of the assay by using the newly available microplate single photon counters. A cDNA encoding for a luciferase is therefore an ideal reporter gene. The use of a luciferase is applicable to many other mechanism-based cellular test systems for pharmaceutical, toxicological and other screening systems.

Jurkat T-cell suspension cultures, stock 1722 are split daily with a dilution of at least 1:2. Final cell density should not exceed $6 \times 10^5$ cells/ml to keep the cells in the logarithmic growth phase. Cells can be seeded at a density $0.5 \times 10^5$ /ml or lower for maintaining stock cultures. Culturing in roller bottles (approx. 10 rpm) is the preferred culture method. The following buffers and reagents are used:

Dulbecco's PBS (phosphate buffered saline)

DEAE-Dextran (MW ca. 500.000), PHARMACIA #17-0350-00 solved at 10 mg/ml in PBS and filtered through 0.2 µm Nalgene filters.

Assay medium: RPMI 1640 without phenol red supplemented with:
+10% FCS inactivated
+1% v/v HEPES buffer (1M)
+1% Penicillin/Streptomycin, GIBCO 043-05070
+0.1% Gentamicin, GIBCO 043-05750

1% Chloroquine (10 mM=5.52 mg/ml in PBS), Sigma #C6628

Wash medium: RPM11640 without phenol red supplemented with:
+1% v/v HEPES buffer (1M)
+1% Penicillin/Streptomycin, GIBCO 043-05070
+0.1% Gentamicin, GIBCO 043-05750

DNA preparations, purified by two cycles of CsCl gradient centrifugation and stored frozen in aliquots at −20° C. (dissolved at 1 mg/ml in $H_2O$)
pCMV-Luc/RRE DNA, #18xx
pEF-cREV DNA, #21xx
pEF-AScREV DNA, #22xx
pCMV-Luc DNA, #3xx luciferase-substrate solution:
2.2 mg AMP (Sigma A1877)
110 mg ATP (Sigma A5394)
385 mg Dithiothreitol
280 µl Luciferin (10 mg/ml in $H_2O$), Sigma L5256 dissolved in 100 ml buffer consisting of:
5 ml HEPES (1M)

20 mg EDTA (Titriplex III)
4 ml Triton® N-101 (nonylphenoxypolyethoxyethanol) (10% in $H_2O$)
4.5 mg Phenylacetic acid, Sigma No. P4514
0.85 mg Oxalic acid, Sigma No. 07626 mg adjusted to 7.8 (2N NaOH. ca 1.1 ml)

Microplates: Packard CulturPlates 6005180 with adhesive seals

Cellfilter Falcon #2340

The assay protocol is as follows:

Preparation of Dilutions:

Pure substances CHC (500 µM in DMSO saturated $H_2O$)) 1:50 to 1:6400 final dilution:
Medium=RPMI 1640 plus additives (see above)
Predilution: 8 µl sample plus 192 µl assay medium (Microplate)
Add 50 µl predilution each in parallel positions to 3 white Packard CulturPlates (B1 through H12)
Blank: 50 µl medium (A1 through A12)
Plates are kept in a $CO_2$-cabinet until addition of cells Broth Of Actinomycetes at 1:200, Fungi at 1:100 and Bacteria at 1:100 final dilutions:
Predilution: 8 µl sample plus 392 µl assay medium=1:50 (Titertek racks), for bacteria and fungi
8 µl sample plus 792 µl assay medium=1:100 (Titertek racks), for actinomycetes
Add 150 µl of predilution each in 3 parallels to white Packard CulturPlates (B1 to H12)
Blank: 50 µl assay medium (A1 to A12)
Plates are kept in a $CO_2$-cabinet until addition of cells Designation of control wells in the primary screen:

| A1, A2 | plate control | medium only, no cells |
|---|---|---|
| A3 to A10 | 'high' control | pCMV-Luc/RRE + pEF-cREV |
| A11, A12 | plate control | medium only, no cells |

Secondary screening (validation) of the positive/toxic hits (1:50 to 1:6400 final dilution for substances):
Predilution: 20 µl sample plus 480 µl assay medium (Titertek racks)
Add 100 µl predilution in duplicates to the wells of rows A (3 to 12) to two Packard CulturPlates in parallel
Add 50 µl of assay medium to all the remaining wells
Dilute columns 3 to 12 by serially transferring 50 µl and discarding the rest after row H.

Preparation of Cells and Transfection Procedure:

Cells as described above, are centrifuged (200 g, 10 min) and washed twice with prewarmed wash medium.

Cells are suspended in prewarmed PBS and counted in a hemacytometer; the cell density is adjusted to $4 \times 10^6$ cells/ml.

DNA-solutions are prepared in prewarmed PBS (2.5 ml/plate, 25 µl/well to be tested):
Add 25 µl DEAE/Dextran pr ml PBS.
Add DNA:
For REV/RRE: 0.60 µl/ml pCMV-Luc/RRE #18xx and 1 µl/ml pEF-cREV #21xx.
For negative controls: 0.60 µl/ml pCMV-Luc/RRE #18xx and 1 µl/ml AScREV #22xx.
For toxicity/unspecific inhibition: 0.60 µl/ml pCMV-Luc #3xx and 1 µl/ml pEF-cREV #21xx.
For toxicity/handling control: 0.60 µl/ml pCMV-Luc #3xx and 1 µl/ml pEF-AScREV #22xx.

Add an equal volume of cell suspension ($4 \times 10^6$ cells/ml) to each of the DNA-solutions.

The DNA/cell suspension is incubated for 10 min. at 37°, shaken gently by hand and incubated for another 10 min.

An equal volume of prewarmed assay medium is added, cells are shaken gently by hand and incubated for another 10 min.

The pelleted cells are resuspended in prewarmed RPMI 1640 plus additives (assay medium) and adjusted to a final concentration of $1 \times 10^6$ cells/ml.

Cells are sucked once through a syringe and filtered through a cell filter immediately before being dispensed to the plates.

50 μl of cell suspension is added to each of the respective wells:

Secondary Jurkat-Rev Assay:

'High' control and substance dilutions: pCMV-luc/RRE+ pEF-cRev in wells A1-H1

Blanks: 50 μl medium in wells A2-D2

'Low' control: pCMV-Iuc/RRE+pEF-AScRev in wells E2-H2

Secondary, Jurkat-Toxicity Assay:

'High' control and substance dilutions: pCMV-luc+pEF-cRev in wells A1-H1

Blanks: 50 μl medium in wells A2-D2

'Handling' control: pCMV-luc+pEF-AScRev in wells E2-H2

Plates axe shaken using a microplate-shaker and stored in the incubator at 37° C. in a 5% $CO_2$ atmosphere for 16–24 hours.

Measurement of Luciferase Activity

After incubation, 100 μl of luciferase substrate solution, to be prepared fleshly every day, is added to each well.

Plates are shaken using a microplate shaker for a few seconds and sealed with an adhesive seal (do NOT use heat-seals).

Plates are counted in a Packard "TopCount Microplate Scintillation and Luminescence Counter" or an equivalent instrument after a count delay of 2 min. for 0.15 min. per well. The temperature of the counting chamber as well as the plate stack should not exceed 22° C., otherwise the half life of the light emission can drop below 4 hours.

The REV-Luc/RRE ('high'-control)- and the Luc (toxicity-control)-background corrected valued should be at last 2000 cps, the AsREV-Luc/RRE (*low*-control) should not exceed 100 cps.

Results

Figure 6:
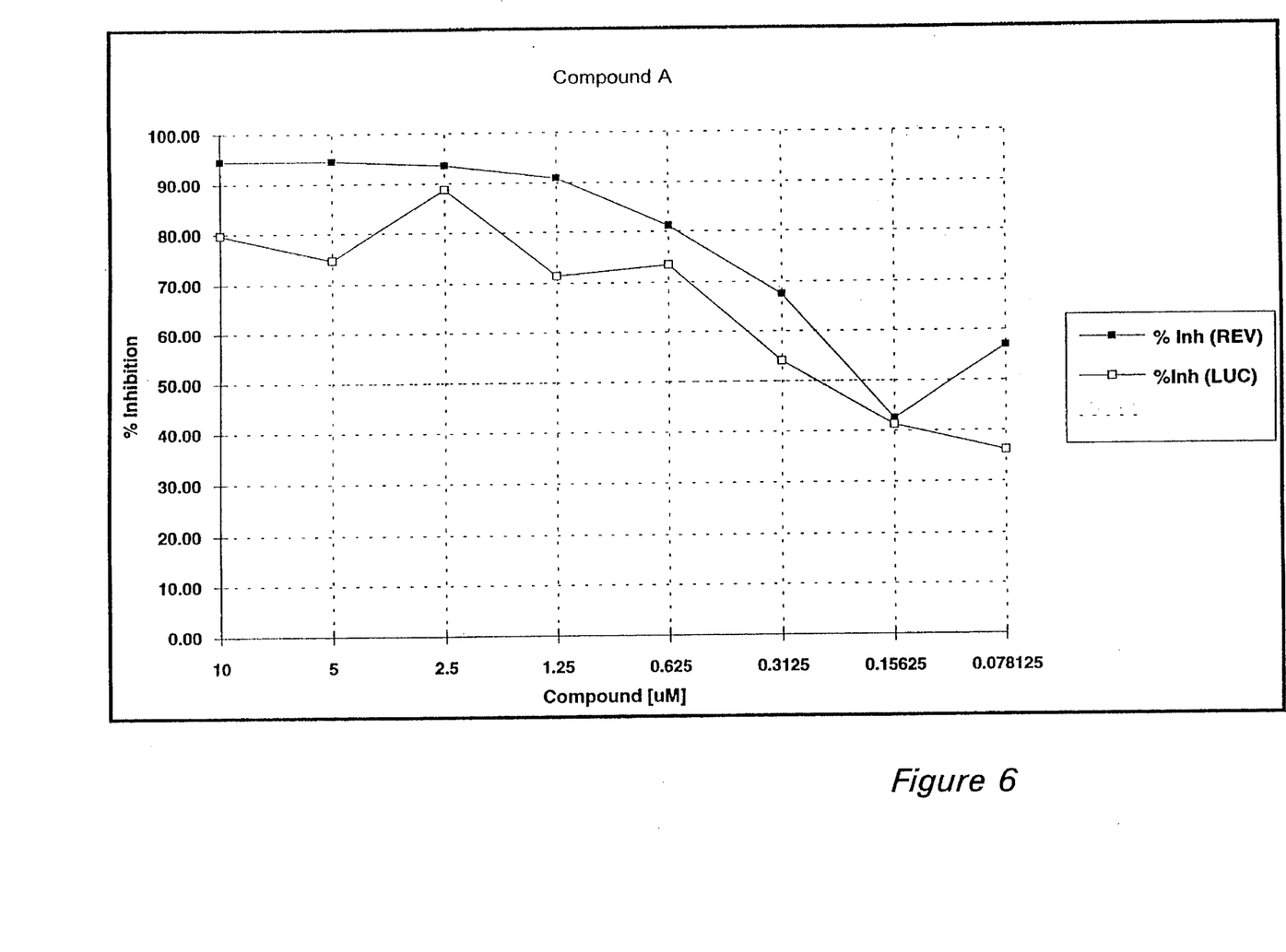
FIG. 6 shows that Compound A is either an unspecific inhibitor of the HIV-rev regulatory protein or is toxic to the cells.
Figure 7:
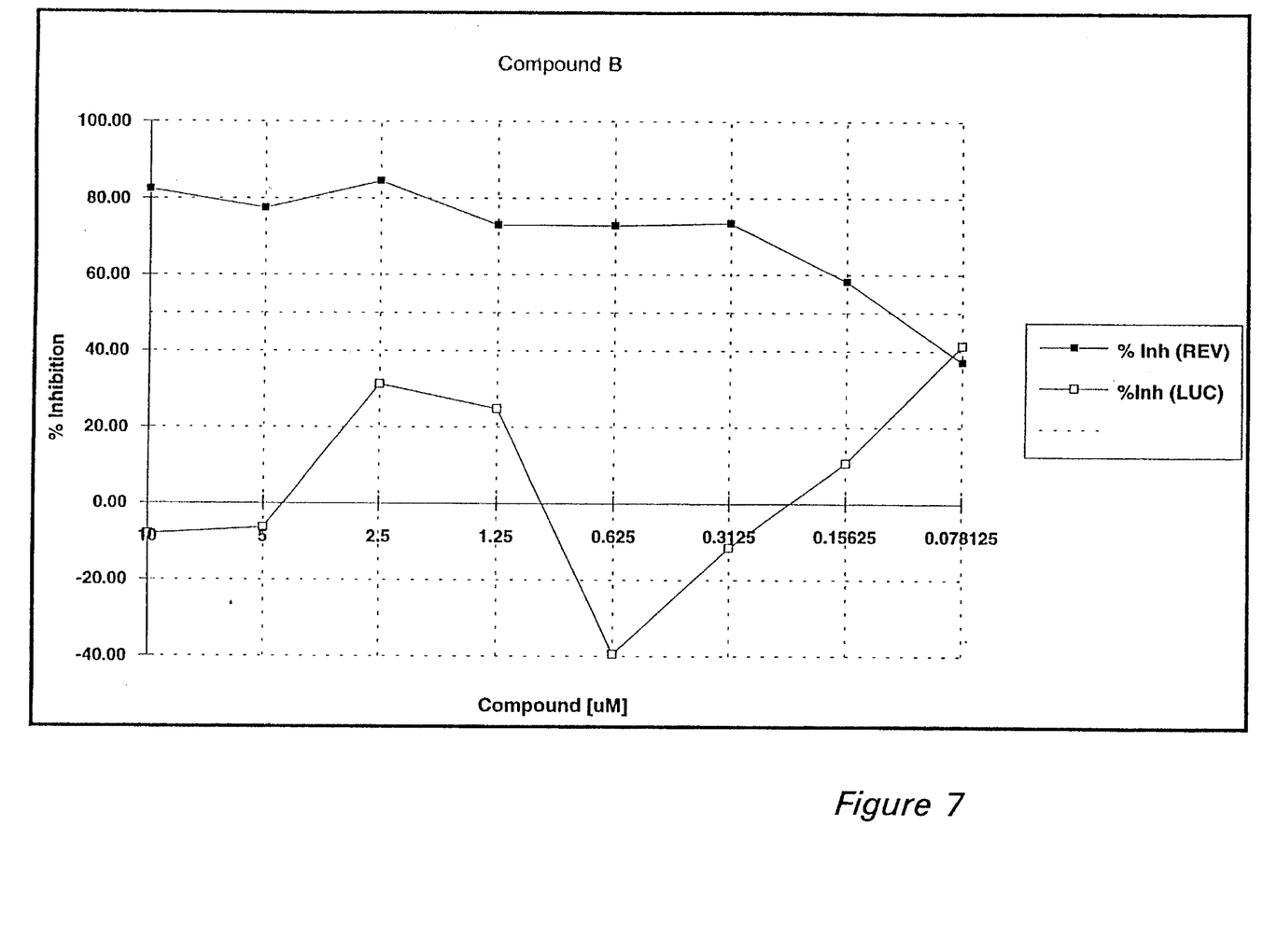
FIG. 7 shows that Compound B is a specific inhibitor of the HIV-rev regulatory protein.

FIGS. 6 and 7 show the results of a large scale compound screening test for compounds which inhibit HIV-rev regulatory protein (RRE). Jurkat cells are co-transfected with two plasmids, pEF-cRev and either pCMV-Luc/RRE or pCMV-Luc. The closed square represents cells which have been transfected with pEFc-REV and pCMV-Luc/RRE. The open square represents cells which have been transfected with pEF-cREV and pCMV-Luc. If a candidate compound inhibits RRE, cells transfected with pEF-cREV and pCMV-Luc/RRE should show a decrease in light production from the luciferase-luciferin reaction compared to cells transfected with pEF-cREV and pCMV-Luc. If a candidate compound does not inhibit RRE, then light production from the luciferase-luciferin reaction should remain unchanged whether cells are transfected with pCMV-Luc/RRE or pCMV-Luc.

FIG. 6 shows the effect of Compound A on RRE. The inhibition curves obtained from cells co-transfected with pEF-cRev and either pCMV-Luc/RRE (closed square) or with pCMV-Luc (open square) is not dramatically different. Compound 6 therefore does not appear to be an inhibitor of RRE. Alternatively, the toxicity of Compound A may prematurely kill the transfected cells before meaningful data can be obtained.

FIG. 7 shows the effect of Compound B on RRE. The inhibition curves obtained from cells co-transfected with pEF-cRev and either pCMV-Luc/RRE (closed square) or with pCMV-Luc (open square) is dramatically different. There is a significant difference in inhibition of RRE between cells transfected with pCMV-Luc/RRE and cells transfected with pCMV-Luc. In cells transfected with pCMV-Luc/RRE, about 0.1 μM Compound B results in 50% inhibition. In cells transfected with pCMV-Luc, Compound B must be present in concentrations greater than 10 μM to obtain 50% inhibition (data not shown).

What is claimed:

1. A method for detecting the presence of luciferase in a biological sample by measuring the luminescence of said sample comprising:

(a) mixing a sample suspected of containing luciferase with a reaction mixture containing luciferin, adenosine triphosphate ("ATP"), cofactors necessary for luciferase catalytic activity, and adenosine monophosphate ("AMP"), the amounts of ingredients in said reaction mixture being selected to produce luminescence having a duration of at least one hour and an intensity that varies substantially linearly with time; and (b) measuring said luminescence produced by said reaction mixture containing said sample.

2. The method of claim 1, wherein the biological sample comprises a cell that produces luciferase.

3. The method of claim 1 wherein 100 ml of the reaction mixture contains from about 0.2 to about 30 mg luciferin, from about 10 to about 300 mg adenosine triphosphate, from about 0.2 to about 30 mg adenosine monophosphate, from about 200 to about 2000 mg dithiothreitol, and from about 10 to about 50 mg ethylenediaminetetraacetic acid.

4. The method of claim 1, wherein said reaction mixture contains a protease inhibitor, a free radical scavenger, a chelating agent, and a detergent to form an admixture.

5. The method of claim 4, wherein the chelating agent is ethylenediaminetetraacetic acid.

6. The method of claim 4, wherein the protease inhibitor is phenylacetic acid or oxalic acid.

7. The method of claim 4, wherein the detergent is nonylphenoxypolyethoxyethanol.

8. The method of claim 4, wherein the free radical scavenger is dithiothreitol.

9. A method for detecting the presence of luciferase in a biological sample comprising:

mixing a sample suspected of containing luciferase with a reaction mixture containing luciferin, a protease inhibitor, adenosine triphosphate, cofactors necessary for luciferase catalytic activity, adenosine monophosphate, and nonylphenoxypolyethoxyethanol to form an admixture the amounts of ingredients in said reaction mixture being selected to produce luminescence having a duration of at least five hours and an intensity that varies substantially linearly with time; and measuring the resulting luminescence of the mixed sample and reaction mixture.

10. The method of claim 9 wherein said protease inhibitor is at least one acid selected from the group consisting of phenylacetic acid and oxalic acid.

11. The method of claim 9 wherein said reaction mixture further includes a chelating agent.

12. The method of claim 11 wherein the chelating agent is ethylenediaminetetraacetic acid.

13. The method of claim 12 wherein said reaction mixture further includes a free radical scavenger.

14. The method of claim 13 wherein said free radical scavenger is dithiothreitol.

15. The method of claim 14 wherein 100 ml of the admixture contains from about 0.2 to about 30 mg luciferin, from about 10 to about 300 mg adenosine triphosphate, from about 0.2 to about 30 mg adenosine monophosphate, from about 200 to about 2000 mg dithiothreitol, from about 10 to about 50 mg ethylenediamine-tetraacetic acid, from about 1 to about 10 mg phenylacetic acid, and from about 0.2 to about 5 mg oxalic acid.

16. A method for detecting the presence of luciferase in a biological sample comprising:

creating a reaction admixture containing luciferin, adenosine triphosphate, cofactors necessary for luciferase catalytic activity, a protease inhibitor, adenosine monophosphate, a detergent, a free radical scavenger, and a chelating agent the amounts of ingredients in said admixture being selected to produce luminscence having a duration of at least five hours and an intensity that varies substantially linearly with time, suspending a biological sample suspected of containing luciferase in a medium containing $Mg^{+2}$, mixing said reaction admixture with said biological sample such that the ratio of $Mg^{+2}$ to said chelating agent is less than about 0.8, and measuring the luminescence.

17. The method of claim 16 wherein said chelating agent is ethylenediaminetetraacetic acid.

18. The method of claim 16 wherein said protease inhibitor is at least one acid selected from a group consisting of phenylacetic acid and oxalic acid.

19. The method of claim 16 wherein said detergent is nonylphenoxypolyethoxyethanol.

20. The method of claim 16 wherein said free radical scavenger is dithiothreitol.

21. A method for detecting the presence of luciferase in a biological sample comprising:

creating an admixture containing luciferin, adenosine triphosphate, cofactors necessary for luciferase catalytic activity, phenylacetic acid, oxalic acid, adenosine monophosphate, dithiothreitol, ethylenediaminetetraacetic acid, and nonylphenoxypolyethoxyethanol, said admixture being substantially free of Coenzyme A, the amounts of ingredients in said admixture being selected to produce luminescence having a duration of at least five hours and an intensity that varies substantially linearly with time, suspending a biological sample suspected of containing luciferase in a medium containing $Mg^{+2}$, mixing said admixture with said biological sample, such that the ratio of $Mg^{+2}$ to ethylenediaminetetraacetic acid is between about 0.4 and about 0.8, and measuring the luminescence.

22. A method for detecting the presence of luciferase in a biological sample comprising:

creating a reaction admixture containing luciferin, adenosine triphosphate, cofactors necessary for luciferase catalytic activity, a protease inhibitor, adenosine monophosphate, a detergent, a free radical scavenger, and ethylenediaminetetraacetic acid, the amounts of ingredients in said admixtuxe being selected to produce luminescence having a duration of at least five hours and an intensity that varies substanially linearly with time, suspending a biological sample suspected of containing luciferase in a medium containing $Mg^{+2}$, mixing said reaction admixture with said medium containing the biological sample, said admixture containing sufficient ethylenediaminetetraacetic acid to remove said $Mg^{+2}$, and measuring the luminescence.

23. A method for detecting the presence of luciferase in a biological sample by measuring the luminescence of said sample comprising;

mixing a sample suspected of containing luciferase with a reaction mixture containing from about 0.2 to about 30 mg luciferin, from about 10 to about 300 mg adenosine triphosphate ("ATP"), from about 0.2 to about 35 mg adenosine monophosphate ("AMP"), from about 200 to about 2000 mg dithiothreitol ("DDT"), from about 10 to about 50 mg ethylenediaminetetraacetic acid ("EDTA"), cofactors necessary for luciferase catalytic activity, and nonylphenoxypolyethoxyethanol the amounts of ingredients in said reaction mixture producing a luminescence having a duration of at least five hours and an intensity that varies substantially linearly with time, suspending a biological sample suspected of containing luciferase in a medium containing $Mg^{+2}$, mixing said reaction admixture with said biological sample such that the ratio of $Mg^{+2}$ to said chelating agent is less than about 0.8, and measuring said luminescence produced by said reaction mixture containing said sample.

24. A method for detecting the presence of luciferase in a biological sample by measuring the luminescence of said sample comprising:

(a) mixing a sample suspected of containing luciferase with a reaction mixture containing luciferin, adenosine triphosphate ("ATP"), cofactors necessary for luciferase catalytic activity, and adenosine monophosphate ("AMP"), the amounts of ingredients in said reaction mixture being selected to produce luminescence having a duration of at least five hours and an intensity that varies substantially linearly with time; and (b) measuring said luminescence produced by said reaction mixture containing said sample.

25. A method for detecting the presence of luciferase in a biological sample by measuring the luminescence of said sample comprising:

(a) mixing a sample suspected of containing luciferase with a reaction mixture containing luciferin, adenosine triphosphate ("ATP"), cofactors necessary for luciferase catalytic activity, and adenosine monophosphate ("AMP"), the amounts of ingredients in said reaction mixture being selected to produce luminescence having a duration of at least eight hours and an intensity that varies substantially linearly with time; and (b) measuring said luminescence produced by said reaction mixture containing said sample.

* * * * *